(12) United States Patent
Veliah et al.

(10) Patent No.: US 11,139,052 B2
(45) Date of Patent: *Oct. 5, 2021

(54) SYSTEMS AND METHODS FOR HEALTH INFORMATION MESSAGES ARCHIVING

(71) Applicant: Open Text Corporation, Waterloo (CA)

(72) Inventors: Shanmugasundaram Veliah, San Jose, CA (US); Lalith G. Subramanian, San Ramon, CA (US)

(73) Assignee: OPEN TEXT CORPORATION, Waterloo (CA)

( * ) Notice: Subject to any disclaimer, the term of this patent is extended or adjusted under 35 U.S.C. 154(b) by 457 days.

This patent is subject to a terminal disclaimer.

(21) Appl. No.: 15/476,428

(22) Filed: Mar. 31, 2017

(65) Prior Publication Data

US 2017/0206331 A1    Jul. 20, 2017

Related U.S. Application Data

(63) Continuation of application No. 13/536,425, filed on Jun. 28, 2012, now Pat. No. 9,639,615.

(51) Int. Cl.
| | | |
|---|---|---|
| *G06F 16/00* | (2019.01) | |
| *G16H 10/60* | (2018.01) | |
| *G06F 16/951* | (2019.01) | |
| *G06F 16/9535* | (2019.01) | |
| *G16H 40/67* | (2018.01) | |
| *G16H 50/70* | (2018.01) | |
| *G16H 30/20* | (2018.01) | |
| *H04L 29/06* | (2006.01) | |

(52) U.S. Cl.
CPC ........... *G16H 10/60* (2018.01); *G06F 16/951* (2019.01); *G06F 16/9535* (2019.01); *G16H 40/67* (2018.01); *G16H 50/70* (2018.01); *G16H 30/20* (2018.01); *H04L 67/42* (2013.01)

(58) Field of Classification Search
CPC ........ G16H 10/60; G16H 50/70; G16H 40/67; G16H 30/20; G06F 19/321; G06F 16/9535; G06F 16/951; G06F 19/3418; H04L 67/42
USPC ........................................................ 707/776
See application file for complete search history.

(56) References Cited

U.S. PATENT DOCUMENTS

| | | |
|---|---|---|
| 7,230,529 B2 | 6/2007 | Ketcherside et al. |
| 9,639,615 B1 | 5/2017 | Veliah |

(Continued)

OTHER PUBLICATIONS

Fan et al. (A hybrid model combining case-based reasoning and fuzzy decision tree for medical data classification, Applied Soft Computing, vol. 11, Jan. 2011, pp. 632-644, Article Available online Dec. 22, 2009) (Year: 2009).*

(Continued)

*Primary Examiner* — Shiow-Jy Fan
(74) *Attorney, Agent, or Firm* — Sprinkle IP Law Group

(57) ABSTRACT

Messages having patient healthcare information are exchanged between various healthcare IT systems. The messages are formatted according to various specific healthcare communication standards. The standards enable communication of the patient healthcare information among the healthcare IT systems. The messages are collected into a repository. Data mining is performed on the collected messages in order to make health-related findings.

19 Claims, 11 Drawing Sheets

(56) References Cited

U.S. PATENT DOCUMENTS

| | | | |
|---|---|---|---|
| 2003/0101076 A1* | 5/2003 | Zaleski | G06Q 50/22 705/2 |
| 2003/0191669 A1* | 10/2003 | Fitzgerald | G06F 19/328 705/2 |
| 2003/0225595 A1* | 12/2003 | Helmus | G06Q 30/04 705/2 |
| 2004/0059598 A1 | 3/2004 | Wellons et al. | |
| 2004/0078236 A1* | 4/2004 | Stoodley | G06Q 50/22 705/2 |
| 2005/0043968 A1 | 2/2005 | Sauerwald | |
| 2006/0117238 A1* | 6/2006 | DeVries | G16H 10/20 714/746 |
| 2006/0265253 A1* | 11/2006 | Rao | G06F 19/321 705/3 |
| 2007/0061393 A1 | 3/2007 | Moore | |
| 2007/0192140 A1 | 8/2007 | Gropper | |
| 2007/0219824 A1* | 9/2007 | Rawlings | G06F 19/328 705/2 |
| 2007/0299688 A1 | 12/2007 | Braz et al. | |
| 2008/0114689 A1* | 5/2008 | Psynik | G06F 19/3418 705/51 |
| 2008/0183495 A1 | 7/2008 | Butterfield et al. | |
| 2008/0208625 A1 | 8/2008 | Joseph | |
| 2009/0080408 A1 | 3/2009 | Natoli | |
| 2009/0099862 A1 | 4/2009 | Fireman et al. | |
| 2009/0164474 A1* | 6/2009 | Noumeir | G06F 19/321 |
| 2009/0259491 A1* | 10/2009 | Busch | G06Q 10/10 705/3 |
| 2010/0131434 A1* | 5/2010 | Magent | G06Q 10/06 706/11 |
| 2010/0256994 A1* | 10/2010 | Eisenberger | G06Q 50/24 705/3 |
| 2011/0119088 A1 | 5/2011 | Gunn | |
| 2011/0213625 A1* | 9/2011 | Joao | G06F 19/328 705/3 |
| 2012/0215799 A1 | 8/2012 | Bohner et al. | |
| 2012/0215860 A1* | 8/2012 | Bohner | G06F 19/321 709/206 |
| 2013/0060787 A1 | 3/2013 | Doshi et al. | |
| 2013/0173719 A1 | 7/2013 | Ahmed et al. | |
| 2014/0358926 A1* | 12/2014 | McGregor | G16H 10/60 707/737 |

OTHER PUBLICATIONS

Office Action for U.S. Appl. No. 13/536,425, dated Sep. 2, 2014, 13 pgs.
Office Action for U.S. Appl. No. 13/536,425, dated Dec. 10, 2014, 18 pgs.
Office Action for U.S. Appl. No. 13/536,425, dated May 21, 2015, 23 pgs.
Office Action for U.S. Appl. No. 13/536,425, dated Oct. 22, 2015, 23 pgs.
Office Action for U.S. Appl. No. 13/536,425, dated Mar. 15, 2016, 22 pgs.
Office Action for U.S. Appl. No. 13/536,425, dated Jul. 28, 2016, 23 pgs.

* cited by examiner

```
HTTP/1.1 200 OK
Server: Apache-Coyote/1.1
Content-Type: application/soap+xml; action="urn:ihe:iti:2007:RegisterDocumentSet-
bResponse";charset=UTF-8
Transfer-Encoding: chunked
Date: Mon, 08 Sep 2008 11:09:15 GMT <?xml version='1.0' encoding='UTF-8'?>
<soapenv:Envelope xmlns:soapenv="http://www.w3.org/2003/05/soap-envelope"
   xmlns:wsa="http://www.w3.org/2005/08/addressing">
   <soapenv:Header>
      <wsa:Action>urn:ihe:iti:2007:RegisterDocumentSet-bResponse</wsa:Action>
      <wsa:RelatesTo>urn:uuid:D9D54C50296A3C11D11220872153270</
wsa:RelatesTo>
   </soapenv:Header>
   <soapenv:Body>
      <rs:RegistryResponse xmlns:rs="urn:oasis:names:tc:ebxml-regrep:xsd:rs:3.0"
         status="urn:oasis:names:tc:ebxml-regrep:ResponseStatusType:Success"/>
   </soapenv:Body>
</soapenv:Envelope>
```

Figure 10B

| MRN | Patient Name | Diagnosis | Allergies | Age | Last Visit | Facility |
|---|---|---|---|---|---|---|
| 8675309 | John Doe | Malignant neoplasm - liver | penicillin | 52 | 2010-10-09 | SMMC |
| ... | ... | ... | ... | ... | ... | ... |
| ... | ... | ... | ... | ... | ... | ... |
| ... | ... | ... | ... | ... | ... | ... |

Figure 11

SYSTEMS AND METHODS FOR HEALTH INFORMATION MESSAGES ARCHIVING

CROSS-REFERENCE TO RELATED APPLICATION

This application is a continuation of, and claims a benefit of priority under 35 U.S.C. 120 of the filing date of U.S. patent application Ser. No. 13/536,425 filed Jun. 28, 2012, entitled "SYSTEMS AND METHODS FOR HEALTH INFORMATION MESSAGES ARCHIVING," the entire contents of which is hereby expressly incorporated by reference for all purposes.

BACKGROUND

The present invention relates to the field of information technology, including, more particularly, to systems and techniques for archiving and mining health information messages exchanged among healthcare systems.

Data mining is the process of analyzing data from different perspectives and summarizing it into useful information. The patterns, associations, or relationships among data can provide knowledge of historical patterns and future trends.

Hospitals and other healthcare organizations typically have many different computer systems used for everything from patient registration to billing to patient tracking to ordering tests. Communication among these computer systems involves a vast amount of information exchange.

It is desirable to archive and mine this information because it can provide insights such as the spread of infectious diseases, health issues of a patient, the health of a population, correlations between treatments and results, and much more.

BRIEF DESCRIPTION OF THE FIGURES

FIG. 10B shows an example of a message structure suitable for use in an XDS framework.

FIG. 11 shows an example of health information message content that may be stored in a repository for data mining.

DETAILED DESCRIPTION

Figure 1:
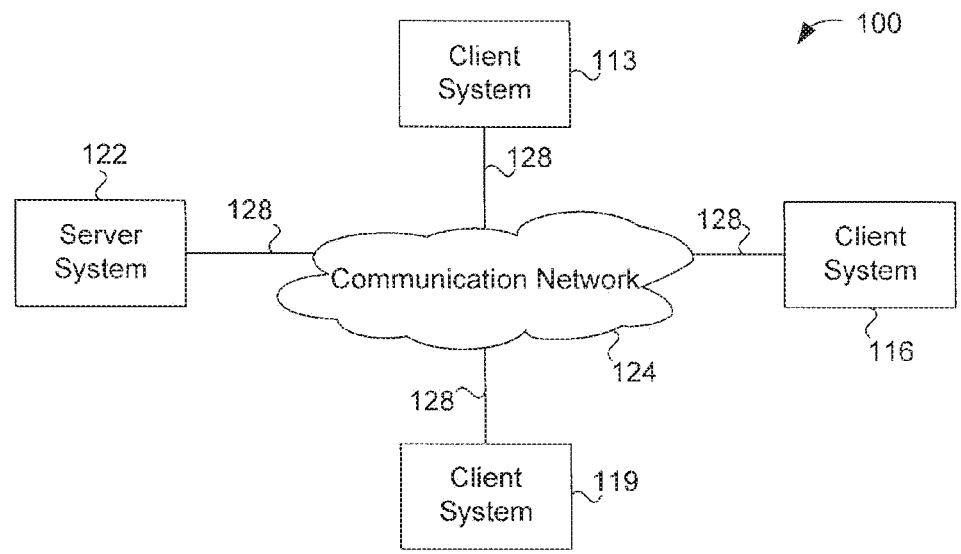
FIG. 1 shows a block diagram of a client-server system and network in which an embodiment of the invention may be implemented.

FIG. 1 is a simplified block diagram of a distributed computer network 100. Computer network 100 includes a number of client systems 113, 116, and 119, and a server system 122 coupled to a communication network 124 via a plurality of communication links 128. There may be any number of clients and servers in a system. Communication network 124 provides a mechanism for allowing the various components of distributed network 100 to communicate and exchange information with each other.

Communication network 124 may itself be comprised of many interconnected computer systems and communication links. Communication links 128 may be hardwire links, optical links, satellite or other wireless communications links, wave propagation links, or any other mechanisms for communication of information. Various communication protocols may be used to facilitate communication between the various systems shown in FIG. 1. These communication protocols may include TCP/IP, HTTP protocols, wireless application protocol (WAP), vendor-specific protocols, customized protocols, and others. While in one embodiment, communication network 124 is the Internet, in other embodiments, communication network 124 may be any suitable communication network including a local area network (LAN), a wide area network (WAN), a wireless network, a intranet, a private network, a public network, a switched network, and combinations of these, and the like.

Distributed computer network 100 in FIG. 1 is merely illustrative of an embodiment and is not intended to limit the scope of the invention as recited in the claims. One of ordinary skill in the art would recognize other variations, modifications, and alternatives. For example, more than one server system 122 may be connected to communication network 124. As another example, a number of client systems 113, 116, and 119 may be coupled to communication network 124 via an access provider (not shown) or via some other server system.

Client systems 113, 116, and 119 typically request information from a server system which provides the information. For this reason, server systems typically have more computing and storage capacity than client systems. However, a particular computer system may act as both a client or a server depending on whether the computer system is requesting or providing information. Additionally, although aspects of the invention have been described using a client-server environment, it should be apparent that the invention may also be embodied in a stand-alone computer system. Aspects of the invention may be embodied using a client-server environment or a cloud-computing environment.

Server 122 is responsible for receiving information requests from client systems 113, 116, and 119, performing processing required to satisfy the requests, and for forwarding the results corresponding to the requests back to the requesting client system. The processing required to satisfy the request may be performed by server system 122 or may alternatively be delegated to other servers connected to communication network 124.

Client systems 113, 116, and 119 enable users to access and query information stored by server system 122. In a specific embodiment, a "Web browser" application executing on a client system enables users to select, access, retrieve, or query information stored by server system 122. Examples of web browsers include the Internet Explorer® browser program provided by Microsoft® Corporation, and the Firefox® browser provided by Mozilla® Foundation, and others.

Figure 2:
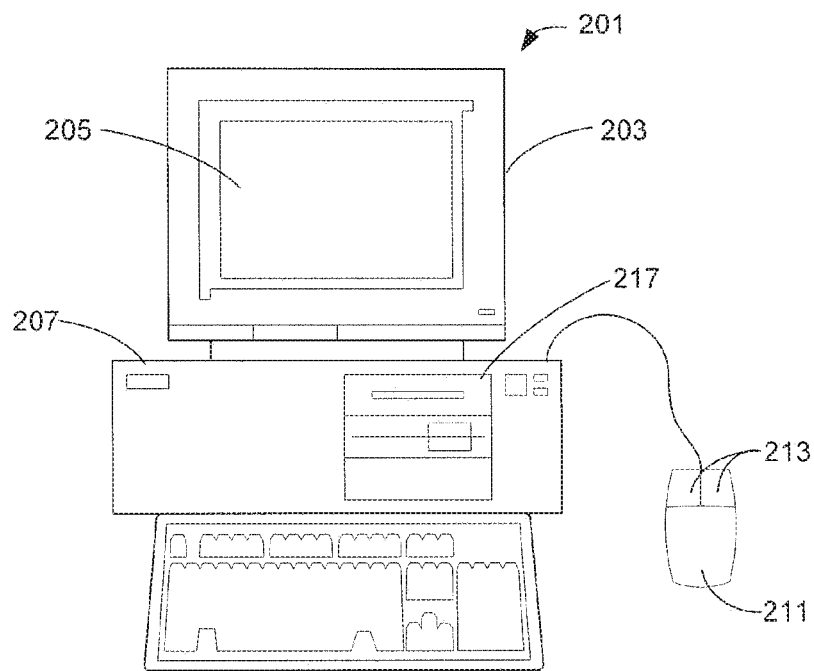
FIG. 2 shows a more detailed diagram of an exemplary client or computer which may be used in an implementation of the invention.

FIG. 2 shows an exemplary client or server system. In an embodiment, a user interfaces with the system through a computer workstation system, such as shown in FIG. 2. FIG. 2 shows a computer system 201 that includes a monitor 203, screen 205, cabinet 207, keyboard 209, and mouse 211. Mouse 211 may have one or more buttons such as mouse buttons 213. Cabinet 207 houses familiar computer components, some of which are not shown, such as a processor, memory, mass storage devices 217, and the like.

Mass storage devices 217 may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc®), flash and other nonvolatile solid-state storage (e.g., USB flash drive), battery-backed-up volatile memory, tape storage, reader, and other similar media, and combinations of these.

A computer-implemented or computer-executable version of the invention may be embodied using, stored on, or associated with computer-readable medium or non-transitory computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on mass storage device 217. The source code of the software may also be stored or reside on mass storage device 217 (e.g., hard disk, magnetic disk, tape, or CD-ROM). As a further example, code may be transmitted via wires, radio waves, or through a network such as the Internet.

Figure 3:
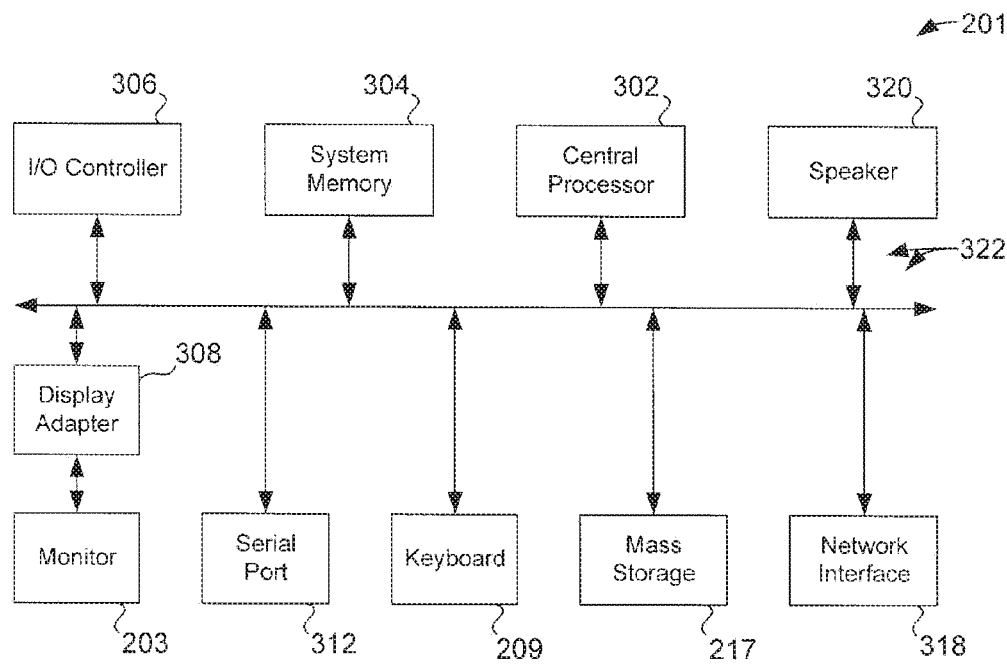
FIG. 3 shows a system block diagram of a client computer system.

FIG. 3 shows a system block diagram of computer system 201. As in FIG. 2, computer system 201 includes monitor 203, keyboard 209, and mass storage devices 217. Computer system 201 further includes subsystems such as central processor 302, system memory 304, input/output (I/O) controller 306, display adapter 308, serial or universal serial bus (USB) port 312, network interface 318, and speaker 320. In an embodiment, a computer system includes additional or fewer subsystems. For example, a computer system could include more than one processor 302 (i.e., a multiprocessor system) or a system may include a cache memory.

Arrows such as 322 represent the system bus architecture of computer system 201. However, these arrows are illustrative of any interconnection scheme serving to link the subsystems. For example, speaker 320 could be connected to the other subsystems through a port or have an internal direct connection to central processor 302. The processor may include multiple processors or a multicore processor, which may permit parallel processing of information. Computer system 201 shown in FIG. 2 is but an example of a suitable computer system. Other configurations of subsystems suitable for use will be readily apparent to one of ordinary skill in the art.

Computer software products may be written in any of various suitable programming languages, such as C, C++, C#, Pascal, Fortran, Perl, Matlab® (from MathWorks), SAS, SPSS, JavaScript®, AJAX, Java®, SQL, and XQuery (a query language that is designed to process data from XML files or any data source that can be viewed as XML, HTML, or both). The computer software product may be an independent application with data input and data display modules. Alternatively, the computer software products may be classes that may be instantiated as distributed objects. The computer software products may also be component software such as Java Beans® (from Oracle Corporation) or Enterprise Java Beans® (EJB from Oracle Corporation). In a specific embodiment, the present invention provides a computer program product which stores instructions such as computer code to program a computer to perform any of the processes or techniques described.

An operating system for the system may be one of the Microsoft Windows® family of operating systems (e.g., Windows 95®, 98, Me, Windows NT®, Windows 2000®, Windows XP®, Windows XP® x64 Edition, Windows Vista®, Windows 7®, Windows CE®, Windows Mobile®), Linux, HP-UX, UNIX, Sun OS®, Solaris®, Mac OS X®, Alpha OS®, AIX, IRIX32, or IRIX64. Other operating systems may be used. Microsoft Windows® is a trademark of Microsoft® Corporation.

Furthermore, the computer may be connected to a network and may interface to other computers using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of the system using a wireless network using a protocol such as Wi-Fi (IEEE standards 802.11, 802.11a, 802.11b, 802.11e, 802.11g, 802.11i, and 802.11n, just to name a few examples). For example, signals from a computer may be transferred, at least in part, wirelessly to components or other computers.

In an embodiment, with a Web browser executing on a computer workstation system, a user accesses a system on the World Wide Web (WWW) through a network such as the Internet. The Web browser is used to download web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 4:
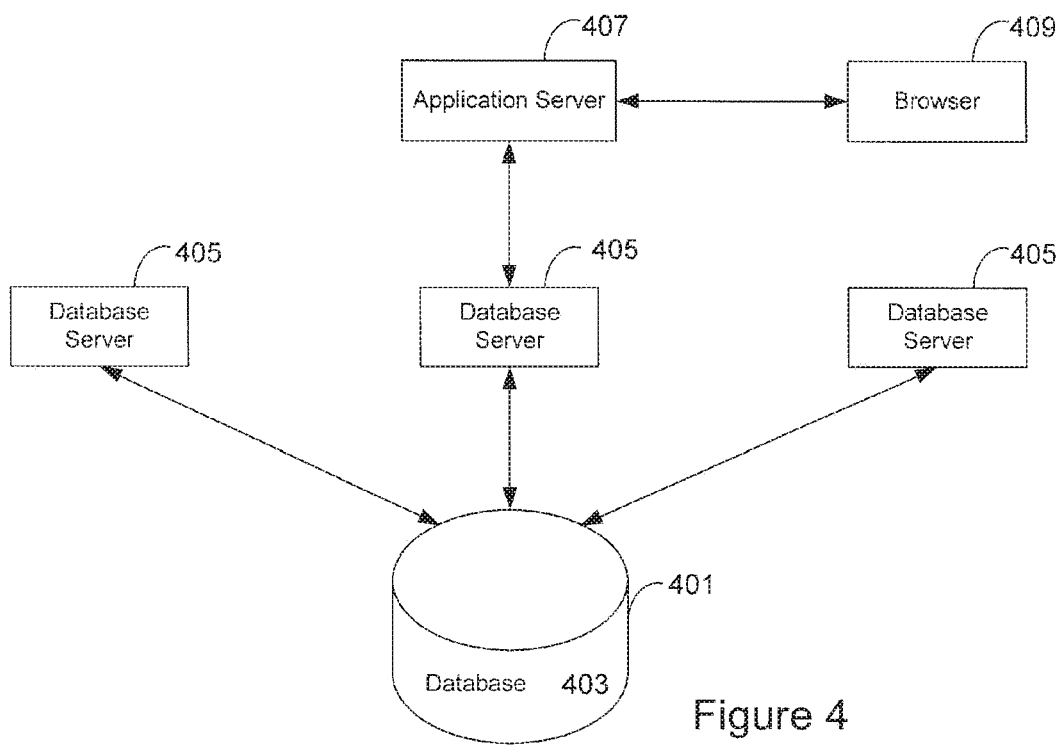
FIG. 4 shows a data source or data service in the form of a database system.

FIG. 4 shows a data source or data service in the form of a database system. A database may be part of a database management system. One suitable database management system architecture is a three-tiered architecture as shown.

In a first tier is the core of a database management system, a central storage 401 that holds or stores a database or repository 403. The database typically resides on one or more hard drives, and is generally part of a larger computer system. The information may be stored in the database in a variety of formats. An example is an Extensible Markup Language (XML) database. An XML database is a data persistence software system that allows data to be stored in XML format. Another example is a relational database management system (RDMS) which uses tables to store the information. Other examples of database systems suitable for use with the present invention include NoSQL database systems (e.g., MongoDB, or Cassandra). A database, however, is merely one example of a data sink suitable for use with the present invention. In other specific embodiments, a file system may be used. Metadata and messages may be written to the file system and a mining system (e.g., Greenplum) may be used. The system can be designed to store information in various kinds of data sinks (file systems, databases, in memory file stores, or others) and use information in that to mine for data too.

In a second tier are database servers 405. The database servers are instances of a program that interacts with the database. Each instance of a database server may, among other features, independently query the database and store information in the database. Depending on the implementation, the database servers 405 may or may not include user-friendly interfaces, such as graphical user interfaces.

In a third tier is an application server 407. There may be multiple application servers. In an implementation, the application server provides the user interfaces to the database servers. By way of example, the application server may be a web application server on the Internet or any other network. The application server may also be a virtual database server or a virtual directory server. The application server may provide user-friendly mechanisms and interfaces for accessing the database through the database servers. In an implementation, a web browser 409 is utilized to access the application server.

Figure 5A:
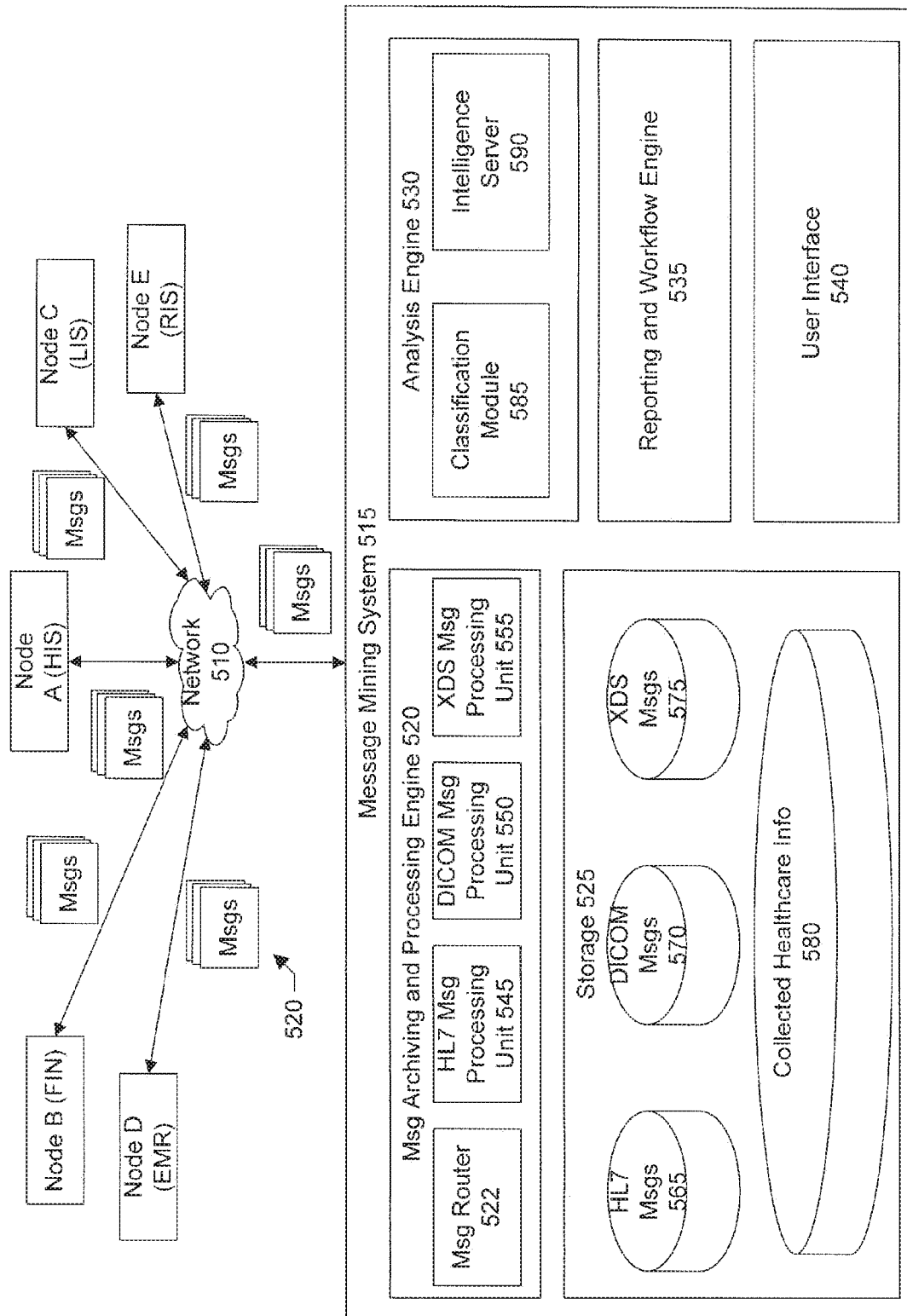
FIG. 5A shows a block diagram of a specific implementation of a system for archiving and mining health information messages.

FIG. 5A shows a block diagram of a specific implementation of a system of the invention. This system includes any number of nodes, such as nodes A-E, having computing information systems configured to manage and exchange healthcare information. As shown in the example of FIG. 5A, each node is connected to or communicates with another node through a network 510. The network may be referred to as a healthcare communication network.

A feature of the invention includes a health information message mining system 515. The system is connected to the healthcare communication network. In a specific implementation, the system collects communications 520 that are exchanged among the nodes. A communication can be a message, file, data object, transaction, or any unit of data transmitted from a node to another node. The system uses data mining techniques on the collected communications in order to make or facilitate health-related findings, inferences, or observations. The system may, based on the findings, generate and send communications to the nodes, physicians, patients, or other users.

The healthcare communication network may be a network as shown in FIG. 1 and described above. Each node computing information system may include servers and clients having computing hardware and software (as shown in FIG. 3 and discussed above) to support the delivery of healthcare services and products. There can be applications for patient care and patient management, financial management, resource management, and so forth.

For example, node A may include a hospital information system ("HIS"). The HIS may include a patient intake or registration system that captures an admitted patient's demographic information (e.g., patient name, address, phone number, date of birth, responses to medical history questionnaires, and the like), health insurance information (e.g., insurance card, insurance group number, insurance plan, or subscriber), primary care physician, signed consent forms, and other registration information. Node B may include a financial system (e.g., billing, or accounting). Node C may include a medical laboratory information system ("LIS"). Node D may include a physician electronic medical record ("EMR") system. Node E may include a radiology information system ("RIS").

The nodes communicate with each other over the network to share health-related information including patient records, lab results (e.g., pathology results), reports (e.g., radiology reports), and the like. When a patient is admitted to a hospital, the hospital information system may create a new patient record. The record may include various details about the patient. This information can be sent to other nodes as appropriate. For example, after visiting with a patient, a doctor may order an x-ray to be performed by the radiology department. The patient details may be sent from the hospital information system to the radiology information system. When the x-ray has been completed the results can be sent from the radiology information system to the physician's EMR system.

Typically, the communication among nodes is performed using certain healthcare specific messaging protocols, formats, structures, or standards, such as Health Level Seven ("HL7"), Digital Imaging and Communications in Medicine ("DICOM"), and Cross Enterprise Document Sharing ("XDS"). HL7, DICOM, and the emerging XDS are the standards for exchanging messages between disparate systems in a healthcare information technology ("IT") landscape. Almost any event in the health setting, be it admitting a patient, discharging a patient, referring a patient, scheduling a office visit, making recommendations for radiological exams, billing, dealing with diagnostic imaging, centralizing health information document such as Continuity of Care Document ("CCD") and Continuity of Care Record ("CCRs"), and others are done through the transmission of messages using one of these three protocols. In another specific embodiment, there can be content with metadata that is not formatted explicitly either as HL7, XDS or DICOM. For example, scanned documents may arrive with a scanned image along with metadata that is not necessarily formatted in one of the three formats specified above.

In a specific implementation, the system archives and mines these documents in order to provide insights such as the spread of infectious diseases. Other features include, for example, tracking the variations of different parameters of a patient over time and using that to determine health issues, correlating the progress of the health of the population over years, and mining of data in DICOM headers in conjunction with other information in HL7 messages that can be used, for example, to correlate treatments with tumor sizes.

In a specific implementation, the messages are captured and a single point of access is provided to the system that can mine the data for information. This system can capture these messages and archive them and provide a single access point for the consuming applications. In addition to archiving, the system may classify these messages along different orthogonal axis like patient medical record number ("MRN"), age, diagnosis, facility, and others to provide a multi-dimensional view of the data.

In a specific implementation, a rendition of the message is de-normalized with regards to the codes that are sent in the messages to facilitate searching and text indexing. De-normalizing the messages may be facilitated through integrating with other systems in the healthcare IT ecosystem or translating it from a static table. This normalization may include looking up demographics from an Enterprise Master Patient Index ("EMPI") to present a view of the data that is augmented with demographic information. The format of the data stored can be optionally tweaked by the end user to conform to a user specified standard.

As shown the example of FIG. 5A, system 515 may include an archiving and processing engine 520, a message router 522, storage or repository 525, an analysis engine 530, a reporting and workflow engine 535, and a user interface 540. The archiving and processing engine includes various processing modules or units such as processing modules 545, 550, and 555. The message router is responsible for forwarding incoming messages to the appropriate processing module. For example, the router can forward HL7 messages to the HL7 processing module, DICOM messages to the DICOM processing module, and XDS messages to the XDS processing module.

The storage includes a database 565 for storing or archiving HL7 messages, a database 570 for storing or archiving DICOM messages, a database 575 for storing or archiving XDS messages, and a database 580 for storing or archiving patient healthcare information collected from the HL7, DICOM, and XDS messages.

Figure 5B:
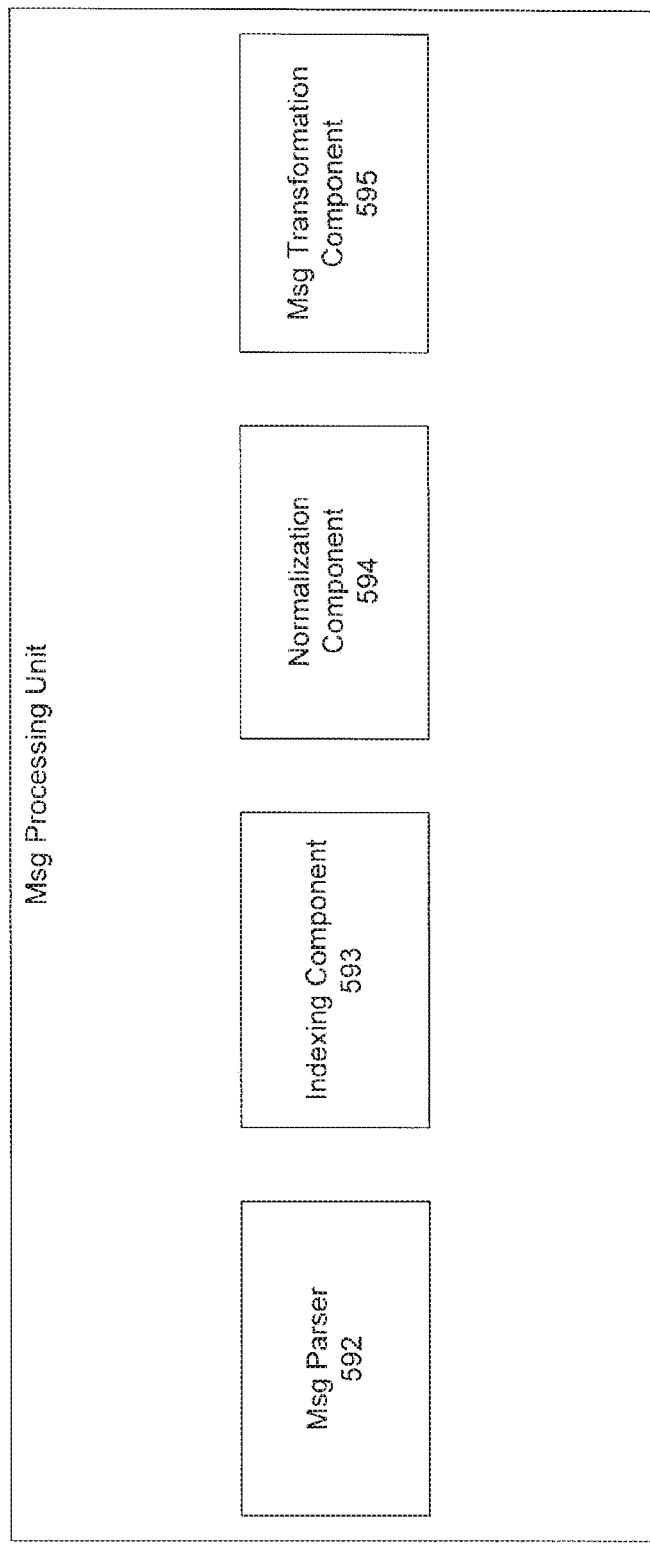
FIG. 5B shows a block diagram of components that may be included in a message processing module.

The processing modules are designed to listen for, intercept, or receive messages formatted according to a particular health information exchange standard. FIG. 5B shows an example of some of the components that may be included in a message processing module or unit. Each module may include a message parser 592, an indexing component 593, a normalization component 594, a message transformation component 595, or combinations of these. The message parser is responsible for analyzing the component parts of a message based on the particular format of the message. The indexing component is responsible for creating an index so that patient healthcare information found in the messages can be queried and retrieved.

The normalization component can convert content found in the message to an equivalent form for storage in database 580. For example, a message may indicate that the drug "Allegra" was prescribed. "Allegra" is a brand name antihistamine pharmaceutical drug. The drug is sometimes prescribed to treat seasonal allergies. The normalization component, upon encountering the term "Allegra" may associate the term with its generic equivalent, e.g., "fexofenadine" for storage in database 580. As another example, the normalization component may associate International Statistical Classification of Diseases and Related Health Problem or IDC codes found in a message with a description of the corresponding disease, disorder, illness, syndrome, injury, or indication. This helps to facilitate searching and text indexing.

The transformation component is responsible for reformatting the message content into a document that can be easily searched and read by humans. In a specific implementation, the message content is transformed into an Extensible Markup Language ("XML") document. Health information content from an HL7 formatted message may be reformatted by the transformation component into an XML document, a text document, a word processing document, a portable document format (PDF) document, or combinations of these.

The analysis engine includes a classification module 585, and an intelligence server 590. The classification module can group and filter the collected patient healthcare information based on any attribute or combination of attributes such as patient medical record number, age, diagnosis, facility, and others. The intelligence server analyzes the patient healthcare information collected from the messages to make health-related findings, observations, inferences, or correlations. The intelligence server may employ, for example, statistical inference, automated reasoning, Bayesian statistics, probability logic, a rules engine, or other.

The reporting and workflow engine can manage the automatic routing of notifications based on the results from the analysis engine. For example, the analysis engine may find that a patient's blood pressure is trending dangerously high. Based on the blood pressure trend, the reporting and workflow engine may send a notification of the trend to the patient. The system can store various user-configurable workflows and workflow templates. In a specific implementation, there is a workflow that monitors patient folders for updates. When an update, such as a new document is in the patient folder, the workflow may trigger a message, such as an HL7 message that is sent to the physician's EMR. The new document may be a patient consent form that has been scanned and placed in the patient folder.

User interface 540 includes a graphical user interface for receiving user input and displaying the results. For example, users may submit queries to the system and view query results through the user interface.

Figures 6, 7:
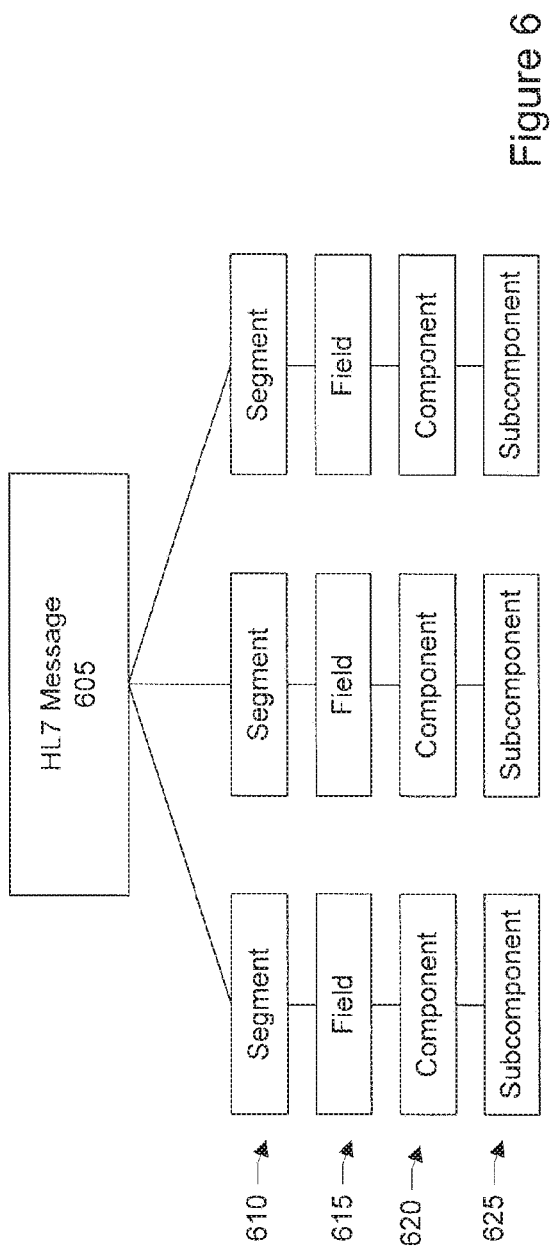
FIG. 6 shows a block diagram of an HL7 message structure.
FIG. 7 shows an example of an HL7 message.

FIG. 6 shows a block diagram of the structure of an HL7 message 605. HL7 is one of several American National Standards Institute (ANSI)-accredited Standards Developing Organizations (SDOs) operating in the health care arena for exchanging clinical and administrative data between medical applications. The "7" refers to the seventh layer in the Open Systems Interconnection ("OSI") model. The seventh OSI layer is the application layer. The HL7 standard defines the format and the content of the messages that medical applications should use when exchanging data with each other.

As shown in FIG. 6, the structure of an HL7 message includes a set of segments 610. Each segment may include one or more predefined fields 615 separated by a pipe character ("|"). A field may be referred to as a composite. Each field includes one or more components 620. A component can include one or more subcomponents 625.

An HL7 message can have any number of segments. A segment occupies a line in the message and is represented or identified by a word or code having three characters. The word or code may include letters, numbers, or both (e.g., alphanumeric). Segments identify the type of information that can be found in the message and group related information. Some examples of segments that may be found in an HL7 message include "MSH," "EVN," "PID," "PV1," "Al1," and "DG1."

The MSH segment is the message header and includes details about the message such as message type, sending, receiving application, date, or acknowledgment required or not. The EVN segment is the event type and is used to communicate trigger event information to receiving applications. The PID segment includes patient information identifying and demographic information that is not likely to change frequently. The PV1 segment includes details of the patient's visit to hospital, such as bed, inpatient/out patient/emergency, visit id, or doctor with whom patient is consulting. The AL1 segment is used to transmit patient allergy information. The DG1 segment is used to transmit the patient diagnosis.

FIG. 7 shows an example of a unit of patient healthcare information formatted according to the HL7 standard. In this example, a message 705 includes seven segments 710. As discussed above and shown in the figure, each segment begins with a three-letter word and occupies a line or row in the message. Each segment is divided into fields separated by the pipe character.

Segment 715 ("PID") includes patient identification data. The segment in this example includes ten fields (some of which are empty). A field may be divided into subfields. For example, a fifth field 720 includes the patient's name. The patient's name is divided into a surname, i.e., "Jones," a first name, i.e., "William," a second name or middle initial, i.e., "A," and a suffix, i.e., "III."

Table A below lists some of the segments and included fields that may be present in an HL7 message.

TABLE A

| Segment | Field |
|---|---|
| PID (Patient Identification) | Patient Name |
| PID | Mother's Maiden Name |
| PID | Date/Time of Birth |
| PID | Sex |
| PID | Race |
| PID | Patient Address |
| PID | Marital Status |
| PID | Birth Place |
| PID | Patient Death Date and Time |
| PID | Patient Death Indicator |
| OBR (Observation Request: information about an exam, diagnostic study/observation, or assessment) | Priority |
| OBR | Requested Date/time |
| OBR | Observation Date/Time |
| OBR | Observation End Date/Time |
| OBR | Collection Volume |
| OBR | Specimen Action Code |
| OBR | Specimen Received Date/Time |
| OBR | Specimen Source |
| OBR | Result Status |
| OBR | Result Copies To |
| OBR | Reason for Study |
| OBR | Principal Result Interpreter |

The segments and fields listed in Table A above are provided merely as an example and Table A is not intended to be a complete listing. An HL7 message may include various other segments and fields not listed in Table A above that the system can analyze. The reference guides "HL7 Messaging Standard Version 2.5.1," "HL7 Version 3 Normative Edition, 2011," and "HL7 Messaging Standard Version 2.7," which are incorporated by reference along with all other references cited in this application, describe other types of HL7 messages, including other segments and fields, which may be mined according to aspects of the present invention.

In a specific implementation, HL7 message processing module 545 (FIG. 5A) is configured to parse an HL7 message in order to identify patient information formatted according to the HL7 standard. The processing module may be configured to scan for particular predefined fields in the HL7 message and copy or extract the field values for storage in the patient healthcare information repository. The information can then be mined to make health-related findings, observations, and so forth.

Figure 8:
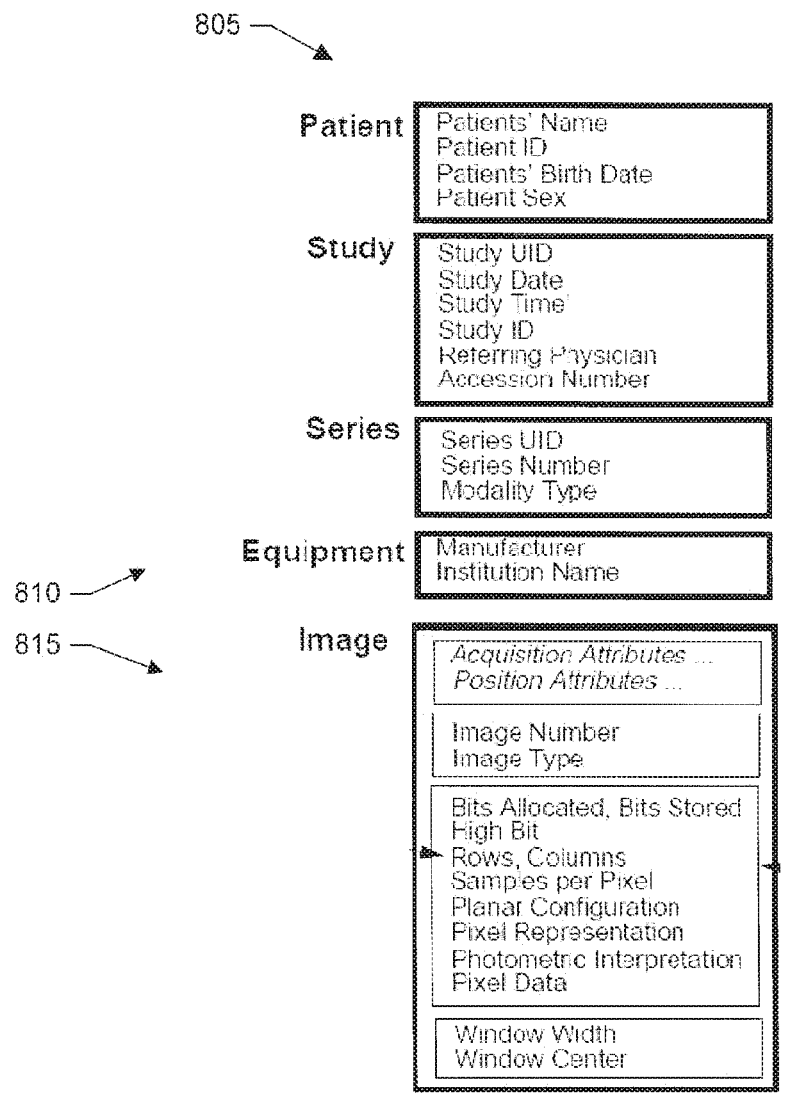
FIG. 8 shows a block diagram of a DICOM file.

FIG. 8 shows a block diagram of a DICOM file or data object ("IOD") 805. DICOM is a standard for handling, storing, printing, and transmitting information in medical imaging. The DICOM standard was developed jointly by the National Electrical Manufacturers Association (NEMA) as well as the American College of Radiology (ACR) to permit interoperability between imaging equipment as well as with other devices. This standard is responsible for governing both the image format as well as the various network protocols required for transmission of medical image information generated during the many healthcare-related imaging "modalities" such as magnetic resonance, nuclear medicine, computed tomography and ultrasound. It includes a file format definition and a network communications protocol. The communication protocol is an application protocol that uses TCP/IP to communicate between systems. DICOM files can be exchanged between two entities that are capable of receiving image and patient data in DICOM format.

DICOM enables the integration of scanners, servers, workstations, printers, and network hardware from multiple manufacturers into a picture archiving and communication system ("PACS"). The different devices may come with DICOM conformance statements which state the DICOM classes they support. DICOM has been widely adopted by hospitals and is making inroads in smaller applications like dentists' and doctors' offices.

Consider the following example. A patient is admitted to a hospital with some chest pains. The attending physician may order an MRI scan, and when this request is recorded on the Hospital Information System (HIS), an electronic request is often transmitted to the Radiology Information System (RIS) located in the imaging centre. This request typically includes information about where the request came from, who ordered it, the details of the patient, the type of imaging modality requested, and so forth. Once the booking is done, the patient then is sent to the imaging centre for the scan. After a scan has been completed, a set of DICOM-compliant images are created from the raw data, and is referred to as a "study." A study may itself include several acquisitions depending on the scan configurations, and each of these acquisitions is referred to as a "series." Each series includes of a number of images, and each of these images is individually referred to as a "DICOM Information Object."

After the scanning procedure has been completed, all the images are transmitted for archival to a Picture Archival and Communication System ("PACS"). The scanned images may be reviewed for quality before being transmitted to a PACS system, and the reviewing technician may order another scan if they are not satisfactory. The archived images can then be retrieved from the PACS system to a workstation for viewing by a radiologist. The radiologist may either view the images directly on the screen, or print these images on film. Later, she may add additional comments about her observations on a report. Once she completes this process, the changes are merged with the original study on the PACS system. An electronic message is also transmitted back to the RIS indicating that the modality request has been completed. Information may also be transmitted back to the originating HIS along with some of the key images to assist in intervention by, for example, a cardiologist if necessary.

As shown in the example of FIG. 8, a DICOM file includes a header portion 810 and an image portion 815. A single DICOM file includes both a header and the image data. As shown in FIG. 8, the header portion includes information organized in groups including information about the patient's name, the type of scan, and image dimensions.

In a DICOM file, typically the first 794 bytes are used for a DICOM format header. The header, as discussed, describes the image dimensions and retains other text information about the scan. The size of this header varies depending on how much header information is stored. The image data follows the header information. Generally, DICOM requires a 128-byte preamble (these 128 bytes are usually all set to zero), followed by the letters "D," "I," "C," and "M."

In a specific implementation, DICOM processing module 550 (FIG. 515) parses a DICOM file to identify patient healthcare information present in the DICOM file. The system stores the identified patient healthcare information from the DICOM file in a patient healthcare information repository. The system applies data mining techniques to the stored healthcare information. FIG. 8 shows an example of some of the patient healthcare information that may be found in a DICOM file (e.g., patient's name, patient ID, patient's birth date, patient sex, study unique identifier ("UI"), study date, study time, study ID, referring physician, and so forth).

Figure 9:
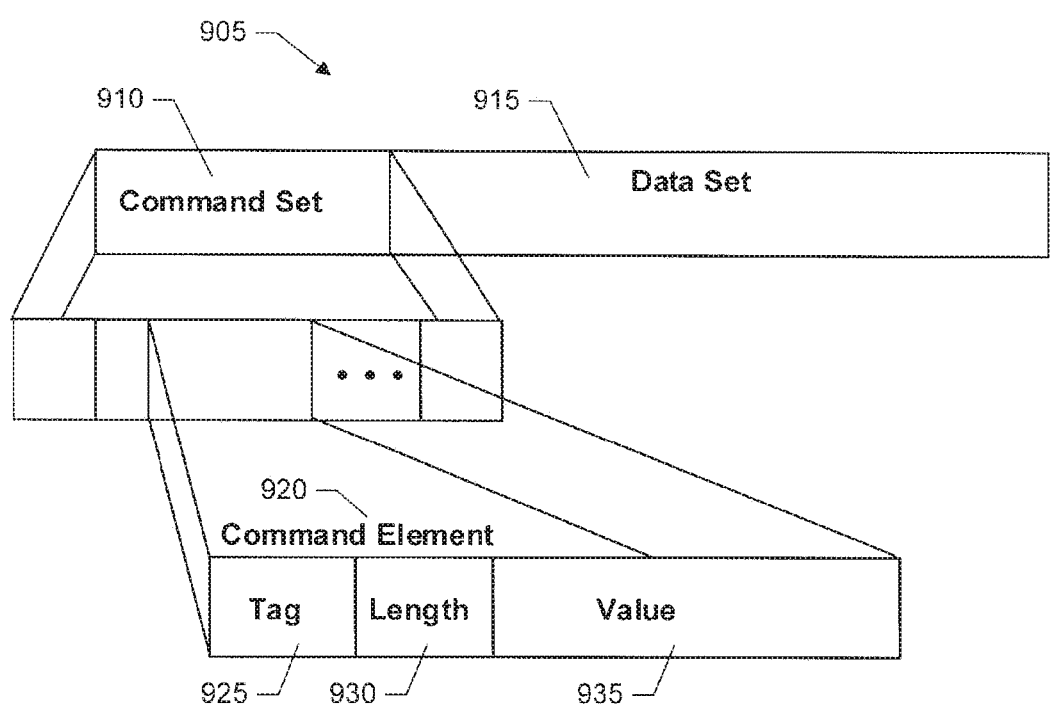
FIG. 9 shows a block diagram of a DICOM message structure.

FIG. 9 shows a block diagram of a DICOM message structure 905. The DICOM message includes a command set 910 followed by a conditional data set 915. Information is communicated across the DICOM network interface in a DICOM message.

The command set is used to indicate the operations/notifications to be performed on or with the data set. A command set is constructed of command elements 920. Command elements include the encoded values for each individual field of the command set per the semantics specified in the DICOM Message Service Element ("DIMSE") protocol. Each command element includes three fields. A first field 925 includes a tag. A second field 930 includes a value length. A third field 935 includes a value field.

The tag includes an ordered pair of 16-bit unsigned integers representing the group number followed by element number. The value length includes a 32-bit unsigned integer representing the explicit length as the number of bytes (even) that make up the value. It does not include the length of the command element tag or value length fields. The value field includes an even number of bytes containing the value or values of the command element.

In a specific implementation, DICOM processing module 550 (FIG. 515) parses a DICOM message to identify one or more tags and corresponding tag values, the tag values being the patient healthcare information. The system stores the patient healthcare information in the patient healthcare information repository. The system applies data mining techniques to the stored healthcare information.

Table B below lists some of the tags and corresponding tag field descriptions that may be present in a DICOM message.

TABLE B

| Tag | Field |
|---|---|
| (0010, 0010) | Patient's Name |
| (0010, 0020) | Patient ID (Primary hospital identification number or code for the patient.) |
| (0010, 1005) | Patient's Birth Name |
| (0010, 1060) | Patient's Mother's Birth Name |
| (0010, 1010) | Patient's Age |
| (0010, 2180) | Occupation |
| (0010, 0050) | Patient's Insurance Plan Code Sequence |
| (0010, 0101) | Patient's Primary Language Code Sequence (The languages that can be used to communicate with the patient.) |
| (0010, 1020) | Patient's Size (Patient's height or length in meters). |
| (0010, 1030) | Patient's Weight |
| (0010, 1040) | Patient's Address |
| (0010, 2000) | Medical Alerts (Conditions to which medical staff should be alerted (e.g. contagious condition, drug allergies, etc.)). |
| (0010, 2110) | Allergies (Description of prior reaction to contrast agents, or other patient allergies or adverse reactions.) |
| (0010, 21A0) | Smoking Status (Indicates whether patient smokes.) |
| (0010, 21 C0) | Pregnancy Status |
| (0038, 0500) | Patient State (Description of patient state (comatose, disoriented, vision impaired, etc.)) |
| (0038, 0502) | Patient Clinical Trial Participation Sequence |
| (0012, 0021) | Clinical Trial Protocol Name |
| (0008, 0080) | Institution Name (Institution where the equipment is located) |
| (0008, 0090) | Referring Physician's Name |
| (0008, 1080) | Admitting Diagnoses Description |
| (0040, 1001) | Requested Procedure ID (Identifier that identifies the Requested Procedure in the Imaging Service Request.) |
| (0040, 1002) | Reason for the Requested Procedure |
| (0020, 000D) | Study Instance UID (Unique identifier to be used to identify the Study) |

The tags and fields listed in Table B above are provided merely as an example and Table B is not intended to be a complete listing. A DICOM message may include various other tags not listed in Table B above that the system can analyze. The 2011 DICOM Standard, which is incorporated by reference, lists other tags that store healthcare information and which may be mined according to aspects of the present invention.

Figure 10A:
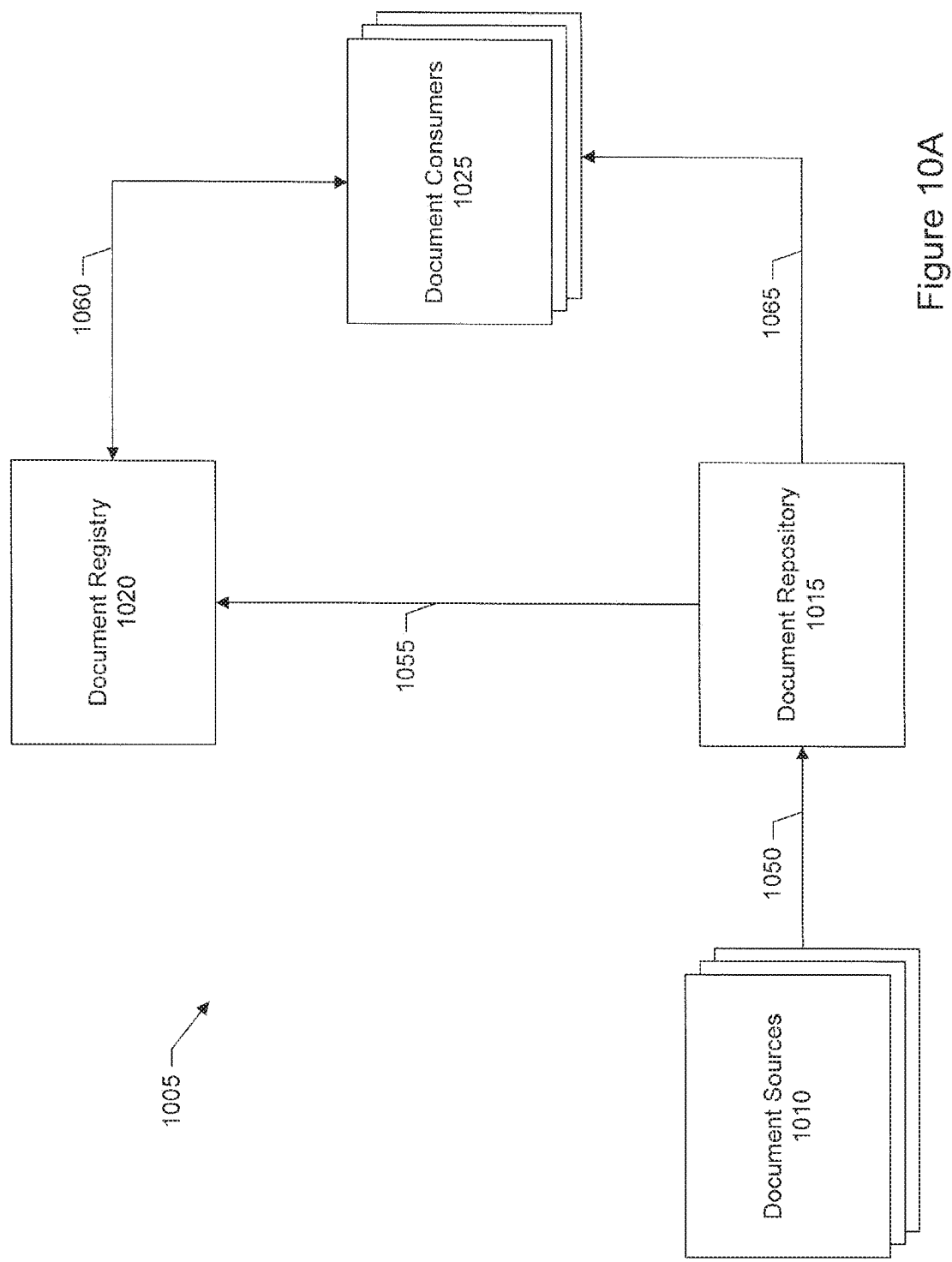
FIG. 10A shows a block diagram of an XDS messaging standard.

FIG. 10A shows a block diagram of an XDS system, framework, profile, or architecture 1005. FIG. 10B shows an example of a message having a structure formatted according to the XDS protocol. Other message examples are available at the IHE Wiki <http://wiki.ihe.net/index.php?title=XDS.b_Implementation#Example_SOAP.2C_MTOM.2C_a nd_MTOM.2FXOP_Messages>, which is incorporated by reference. The XDS system is promoted by Integrating the Healthcare Enterprise ("THE"). IEEE promotes the use of standards, such as DICOM and HL7, to develop workflow solutions for the healthcare enterprise. XDS is designed to facilitate the sharing of clinical documents between institutions. As shown in FIG. 10A, the main components of an XDS system includes one or more document sources 1010, a document repository 1015, a document registry 1020, and one or more document consumers 1025.

A flow for the XDS system may be as follows. In a step 1050, the document source (e.g., document author or creator) provides or publishes the clinical document to the document repository. Examples of clinical documents include a radiology report with referenced images, a discharge summary, or a medication list.

The document repository is responsible for storing the documents. In a step 1055, the repository passes to the document registry document metadata and a pointer to the location in the repository where the document is stored. In an implementation, the document registry maintains an index of published documents. The registry includes a set of document attributes or properties for each document stored. Some examples of attributes include patient name, document type, and storage location.

The document consumer may be a web browser or other interface. The document consumer, under the direction of, for example, a user, may query 1060 the registry to, for example, locate records of a particular type for a particular patient. The desired document can then be retrieved 1065 from the repository.

FIG. 11 shows an example of some of the patient healthcare information that may be stored in patient healthcare information repository 580 (FIG. 5A). In a specific implementation, a system of the invention collects or aggregates patient information from HL7 messages, DICOM files, DICOM messages, XDS document repositories, XDS document registries, or combinations of these into the patient healthcare information repository 580. In a specific implementation, the healthcare information is copied into the repository and the original data (e.g., original HL7 message) is not modified. This helps to ensure the integrity of the original data.

Figure 12:
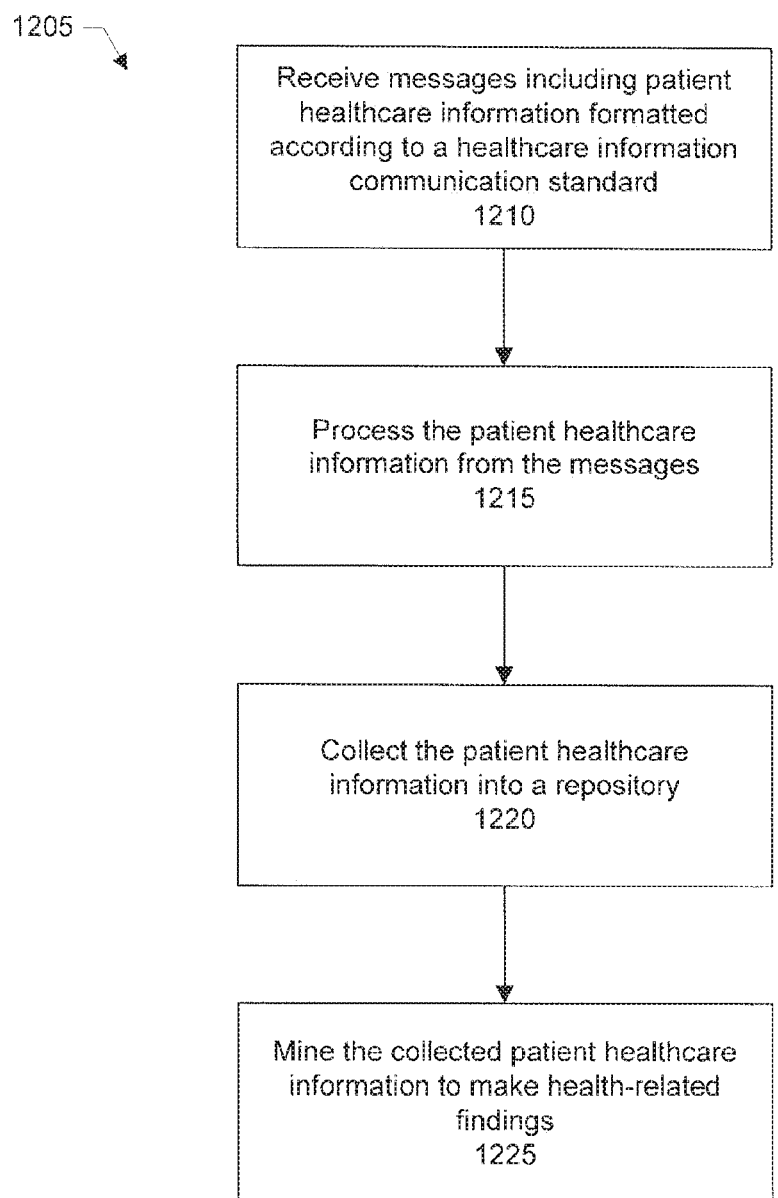
FIG. 12 shows an overall flow for collecting and mining health information messages.

FIG. 12 shows an overall flow 1205 for mining patient healthcare information stored in the patient healthcare information repository. Some specific flows are presented in this application, but it should be understood that the process is not limited to the specific flows and steps presented. For example, a flow may have additional steps (not necessarily described in this application), different steps which replace some of the steps presented, fewer steps or a subset of the steps presented, or steps in a different order than presented, or any combination of these. Further, the steps in other implementations may not be exactly the same as the steps presented and may be modified or altered as appropriate for a particular process, application or based on the data.

In a step 1210, the system receives messages. The messages include patient healthcare information formatted according to a healthcare information communication standard. For example, the information may be formatted according to the HL7 standard, the DICOM standard, or XDS standard.

In a step 1215, the system processes the patient healthcare information from the messages. In a specific implementation, processing includes normalizing the healthcare information. In a specific implementation, a method for normalizing includes scanning message content to identify a first name of a drug recorded in the message content. The method further includes identifying a second name of the drug not recorded in the message content and associating the second name with the first name. One of the first or second names is a brand name of the drug. The other of the first or second names is a generic name of the drug. The normalizing allows returning search results for both the brand and generic drug names.

In another specific implementation, processing includes indexing message content.

The indexing can allow for fast retrieval of messages in response to a search query. Some examples index data structures that may be maintained by the system include a suffix tree, inverted index, citation index, ngram index, or document-term matrix.

In another specific implementation, processing includes transforming or reformatting message content to an XML document or a text-based document to facilitate searching.

In a step 1220, the system collects the patient healthcare information in a repository. The repository may include data from HL7 formatted messages, data from DICOM formatted messages, data from XDS formatted messages, free text messages like a scanned images with metadata, or combinations of these.

In a step 1225, the system mines the collected healthcare information to make health-related findings. The data mining may include cluster analysis, anomaly detection, associating rule mining, spatial indexes, predictive analytics, or combinations of these.

In a specific implementation, the system can act on the collected healthcare information. For example, in a specific implementation, the system provides a health monitoring or notification service. The system may analyze messages associated with a particular patient, discover that the patient's blood pressure is trending dangerously high, and send out notifications to the patient, the patient's doctor or both to inform them of the findings. The system may send out periodic notifications (e.g., HL7 messages, email messages) or surveys to the patient in order to assess the patient's current health state. In this specific implementation, a feature of the system includes monitoring the changes to the patient (via the messages) and routing them through a workflow for actions to be taken based on rules. There can be human intervention like alerting a doctor or sending an email to the patient to come for a visit, making an appointment with the HIS system on the patient behalf, and so forth.

In another specific implementation, the system provides surveillance to detect the spread of infectious diseases. For example, the system can collect messages associated with patients entering the hospital and look for signs or other indications of an epidemic or disease outbreak. For example, the system can monitor the messages exchanged between the various system of a health information network to determine a number of times a particular disease has been recorded in the messages. If the number of times is greater than a predetermined threshold value, the system may generate an alert. If the number of times within a particular time period is greater than a threshold frequency, the system may generate an alert.

In another specific implementation, the system provides a predictive analytical service. In this specific implementation, the system analyzes messages collected over a period of time and which identify a particular patient. Based on the analysis, the system makes a prediction of the patient's prognosis.

In another specific implementation, the system includes a set of classification rules for automatically classifying the messages. There can be any number of different orthogonal axes. For example, the system may classify messages based on the identified patient in the messages, the ailment recorded in the messages, the medication recorded in the messages, the symptoms recorded in the messages, or combinations of these.

In another specific implementation, the system can make correlations or inferences based on analyzing the patient health information recorded in the messages.

In another specific implementation, the system provides a configuration interface. Through the configuration interface, users (e.g., administrators) can specify the message fields whose values are to be captured. For example, one hospital may specify that values in fields X, Y, and Z in the messages are to be captured and stored in the repository. Another hospital may specify that values in fields A, B, and C are instead to be captured and stored. This feature allows individual hospitals to tailor or customize the system according to their needs.

In the description above and throughout, numerous specific details are set forth in order to provide a thorough understanding of an embodiment of this disclosure. It will be evident, however, to one of ordinary skill in the art, that an embodiment may be practiced without these specific details. In other instances, well-known structures and devices are shown in block diagram form to facilitate explanation. The description of the preferred embodiments is not intended to limit the scope of the claims appended hereto. Further, in the methods disclosed herein, various steps are disclosed illustrating some of the functions of an embodiment. These steps are merely examples, and are not meant to be limiting in any way. Other steps and functions may be contemplated without departing from this disclosure or the scope of an embodiment.

What is claimed is:

1. A method of mining healthcare communication messages transmitted over a healthcare network comprising:

receiving from the healthcare network a plurality of first messages, the plurality of first messages comprising first patient healthcare information formatted according to a first healthcare communication standard;

archiving the plurality of received first messages in a first database associated with the first healthcare communication standard, wherein each of the plurality of received first messages is archived in an unmodified form;

automatically classifying the plurality of first messages according to a stored set of classification rules, wherein the classifying is based on a plurality of different orthogonal axes;

obtaining the first patient healthcare information by parsing the plurality of received first messages based on the first healthcare communication standard to extract from the plurality of received first messages field values as defined by the first healthcare communication standard which comprise the first patient healthcare information;

collecting, in a repository which is separate from the first database associated with the first healthcare communication standard, the first patient healthcare information by copying the field values of the obtained first patient healthcare information into the repository;

mining the field values of the collected first patient healthcare information extracted from the plurality of received first messages to make first health-related findings by identifying a plurality of messages associated with a particular patient, analyzing, for the collected first patient healthcare information extracted from the plurality of messages associated with the particular patient, ones of the field values corresponding to a selected characteristic of the particular patient, and determining a trend of the analyzed field values; and communicating the first health-related findings to a user via a communication interface.

2. The method of claim 1, wherein communicating the first health-related findings to the user comprises, in response to determining the trend, transmitting a notification to at least one of the particular patient and a doctor of the particular patient.

3. The method of claim 1, wherein mining the field values of the collected first patient healthcare information extracted from the plurality of received first messages to make the first health-related findings comprises monitoring changes to the particular patient indicated by the plurality of messages associated with the particular patient and routing the plurality of messages associated with the particular patient through a workflow which is configured to take actions based on a corresponding set of rules.

4. The method of claim 1, wherein the plurality of different orthogonal axes include two or more of: patient identifiers in the messages; ailments recorded in the messages; medications recorded in the messages; and symptoms recorded in the messages.

5. The method of claim 1, wherein mining the field values of the collected first patient healthcare information extracted from the plurality of received first messages to make the first health-related findings comprises collecting a plurality of messages associated with a particular patient over a period of time, analyzing the collected plurality of messages associated with the particular patient, and generating a prediction of the particular patient's prognosis.

6. The method of claim 1, wherein mining the field values of the collected first patient healthcare information extracted from the plurality of received first messages to make the first health-related findings comprises:

monitoring the plurality of first messages;

identifying indications of a particular disease in the plurality of first messages;

determining whether the indications of the particular disease in the plurality of first messages meet a threshold condition;

in response to determining that the indications of the particular disease in the plurality of first messages meet the threshold condition, generating an alert indicative of an outbreak of the particular disease.

7. The method of claim 6, wherein the threshold condition comprises detecting a threshold number of the indications of the particular disease within a selected time period.

8. A computer program product, comprising a non-transitory computer-readable medium having a computer-readable program code embodied therein, the computer-readable program code adapted to be executed by one or more processors to implement a method comprising:

receiving from a healthcare network a plurality of first messages, the plurality of first messages comprising first patient healthcare information formatted according to a first healthcare communication standard;

archiving the plurality of received first messages in a first database associated with the first healthcare communication standard, wherein each of the plurality of received first messages is archived in an unmodified form;

automatically classifying the plurality of first messages according to a stored set of classification rules, wherein the classifying is based on a plurality of different orthogonal axes;

obtaining the first patient healthcare information by parsing the plurality of received first messages based on the first healthcare communication standard to extract from the plurality of received first messages field values as defined by the first healthcare communication standard which comprise the first patient healthcare information;

collecting, in a repository which is separate from the first database associated with the first healthcare communication standard, the first patient healthcare information by copying the field values of the obtained first patient healthcare information into the repository;

mining the field values of the collected first patient healthcare information extracted from the plurality of received first messages to make first health-related findings by identifying a plurality of messages associated with a particular patient, analyzing, for the collected first patient healthcare information extracted from the plurality of messages associated with the particular patient, ones of the field values corresponding to a selected characteristic of the particular patient, and determining a trend of the analyzed field values; and communicating the first health-related findings to a user via a communication interface.

9. The computer program product of claim 8, wherein communicating the first health-related findings to the user comprises, in response to determining the trend, transmitting a notification to at least one of the particular patient and a doctor of the particular patient.

10. The computer program product of claim 8, wherein mining the field values of the collected first patient healthcare information extracted from the plurality of received first messages to make the first health-related findings comprises monitoring changes to the particular patient indicated by the plurality of messages associated with the particular patient and routing the plurality of messages associated with the particular patient through a workflow which is configured to take actions based on a corresponding set of rules.

11. The computer program product of claim 8, wherein the plurality of different orthogonal axes includes two or more of: patient identifiers in the messages; ailments recorded in the messages; medications recorded in the messages; and symptoms recorded in the messages.

12. The computer program product of claim 8, wherein mining the field values of the collected first patient healthcare information extracted from the plurality of received first messages to make the first health-related findings comprises collecting a plurality of messages associated with a particular patient over a period of time, analyzing the collected plurality of messages associated with the particular patient, and generating a prediction of the particular patient's prognosis.

13. The computer program product of claim 8, wherein mining the field values of the collected first patient healthcare information extracted from the plurality of received first messages to make the first health-related findings comprises:
   monitoring the plurality of first messages;
   identifying indications of a particular disease in the plurality of first messages;
   determining whether the indications of the particular disease in the plurality of first messages meet a threshold condition;
   in response to determining that the indications of the particular disease in the plurality of first messages meet the threshold condition, generating an alert indicative of an outbreak of the particular disease.

14. A system for mining healthcare communication messages, the system comprising:
   a processor-based database management system executed on a computer system and configured to:
   receive from a healthcare network a plurality of first messages, the plurality of first messages comprising first patient healthcare information formatted according to a first healthcare communication standard;
   archive the plurality of received first messages in a first database associated with the first healthcare communication standard, wherein each of the plurality of received first messages is archived in an unmodified form;
   automatically classify the plurality of first messages according to a stored set of classification rules, wherein the classifying is based on a plurality of different orthogonal axes;
   obtain the first patient healthcare information by parsing the plurality of received first messages based on the first healthcare communication standard to extract from the plurality of received first messages field values as defined by the first healthcare communication standard which comprise the first patient healthcare information;
   collect, in a repository which is separate from the first database associated with the first healthcare communication standard, the first patient healthcare information by copying the field values of the obtained first patient healthcare information into the repository;
   mine the field values of the collected first patient healthcare information extracted from the plurality of received first messages to make first health-related findings by identifying a plurality of messages associated with a particular patient, analyzing, for the collected first patient healthcare information extracted from the plurality of messages associated with the particular patient, ones of the field values corresponding to a selected characteristic of the particular patient, and determining a trend of the analyzed field values; and
   communicate the first health-related findings to a user via a communication interface.

15. The system of claim 14, wherein the processor-based database management system is configured to
   communicate the first health-related findings to the user by, in response to determining the trend, transmitting a notification to at least one of the particular patient and a doctor of the particular patient.

16. The system of claim 14, wherein the processor-based database management system is configured to mine the field values of the collected first patient healthcare information extracted from the plurality of received first messages to make the first health-related findings by monitoring changes to the particular patient indicated by the plurality of messages associated with the particular patient and routing the plurality of messages associated with the particular patient through a workflow which is configured to take actions based on a corresponding set of rules.

17. The system of claim 14, wherein the plurality of different orthogonal axes include two or more of: patient identifiers in the messages; ailments recorded in the messages; medications recorded in the messages; and
   symptoms recorded in the messages.

18. The system of claim 14, wherein the processor-based database management system is configured to mine the field values of the collected first patient healthcare information extracted from the plurality of received first messages to make the first health-related findings by collecting a plurality of messages associated with a particular patient over a period of time, analyzing the collected plurality of messages associated with the particular patient, and generating a prediction of the particular patient's prognosis.

19. The system of claim 14, wherein the processor-based database management system is configured to mine the field values of the collected first patient healthcare information extracted from the plurality of received first messages to make the first health-related findings by:
   monitoring the plurality of first messages;
   identifying indications of a particular disease in the plurality of first messages;
   determining whether the indications of the particular disease in the plurality of first messages meet a threshold condition;
   in response to determining that the indications of the particular disease in the plurality of first messages meet the threshold condition, generating an alert indicative of an outbreak of the particular disease.

* * * * *